(12) United States Patent
Deschamps et al.

(10) Patent No.: US 8,765,184 B2
(45) Date of Patent: Jul. 1, 2014

(54) METHOD FOR PREPARING PHARMACEUTICAL COMPOSITIONS COMPRISING FINE PARTICLES OF ACTIVE SUBSTANCE

(75) Inventors: Frantz Deschamps, Nancy (FR); Jennifer Jung, Dieulouard (FR); Fabrice Leboeuf, Saint Max (FR)

(73) Assignee: Stanipharm, Champigneulles (FR)

( * ) Notice: Subject to any disclaimer, the term of this patent is extended or adjusted under 35 U.S.C. 154(b) by 153 days.

(21) Appl. No.: 13/262,538

(22) PCT Filed: Mar. 30, 2010

(86) PCT No.: PCT/FR2010/000266
§ 371 (c)(1),
(2), (4) Date: Sep. 30, 2011

(87) PCT Pub. No.: WO2010/112702
PCT Pub. Date: Oct. 7, 2010

(65) Prior Publication Data
US 2012/0021021 A1 Jan. 26, 2012

(30) Foreign Application Priority Data

Mar. 31, 2009 (FR) .................................... 09 01578

(51) Int. Cl.
*A61K 9/14* (2006.01)
(52) U.S. Cl.
USPC ............ 424/489; 424/490; 424/493; 424/494
(58) Field of Classification Search
USPC .................. 424/465–484, 489, 490, 493, 494
See application file for complete search history.

(56) References Cited

U.S. PATENT DOCUMENTS 4,582,731 A 4/1986 Smith
2002/0189454 A1* 12/2002 Perrut .............................. 95/274

FOREIGN PATENT DOCUMENTS

WO 0143853 A1 6/2001
WO 2009034409 A2 3/2009

OTHER PUBLICATIONS

Robertson et al (Recrystallization of Organic Compounds Using Near Critical Carbon Dioxide, The 4th International Symposium on Supercritical Fluids, May 11-14, Sendai, Japan, 1997, p. 47-50).*
International Search Report of PCT/FR2010/000266; Jul. 6, 2010; Sophie Muller.
Rodier et al., "La generation de solides divises par voie supercritique: principes de base, considerations sur l'etat d'avancement des recherches", Cahiers de Formulation, 2008, vol. 14, pp. 90-105, English abstract is provided.
Jung et al., "High Pressure in Venice", Chemical Engineering Transactions, 2002, vol. 2, pp. 459-463.
Jung et al., "Particle design using supercritical fluids: Literature and patent survey", Journal of Supercritical Fluids, 2001, vol. 20, pp. 179-219.
Kesisoglou et al., "Nanosizing—Oral formulation development and biopharmaceutical evaluation", Advanced Drug Delivery Review, 2007, vol. 59, pp. 631-644.
Turk, Michael, "Manufacture of submicron drug particles with enhanced dissolution behaviour by rapid expansion processes", Journal of Supercritical Fluids, 2009, vol. 47, pp. 537-545.
Robertson et al. "Recrystallisation of Organic Compounds Using Near Critical Carbon Dioxide", Proceedings of the 4th International Symposium on Supercritical Fluids, May 11-14 Sendai, Japan 1997.
Lemmon et al., "Thermophysical Properties of Fluid Systems", WebBook of Chemistry NIST, Standard Reference Database NIST No. 69, Eds. P.J. Linstrom and W.G. Mallard, National Institute of Standards and Technology, Gaithersburg MD, 20899, http://webbook.nist.gov., 2011.
International Preliminary Report of Patentability, from corresponding PCT application, Jul. 2010.

* cited by examiner

*Primary Examiner* — Michael G Hartley
*Assistant Examiner* — Micah-Paul Young
(74) *Attorney, Agent, or Firm* — Young & Thompson (57) ABSTRACT

The present invention relates to a method for preparing solid pharmaceutical compositions comprising fine particles of at least one active substance, dispersed on and (or) within a divided solid. This method is characterized in that a solution is formed which comprises at least one active substance in a fluid at supercritical pressure, said solution then being expanded in a chamber under temperature and pressure conditions for which a part of said fluid is in the liquid state at the time of the expansion, said fluid thus expanded being brought into contact with a divided solid in said chamber.

16 Claims, 9 Drawing Sheets

METHOD FOR PREPARING PHARMACEUTICAL COMPOSITIONS COMPRISING FINE PARTICLES OF ACTIVE SUBSTANCE

CROSS-REFERENCE

The present application is the United States National Stage of PCT/FR2010/00266 filed Mar. 30, 2010. The present application claims the benefit of priority to French patent application no. 09 01578 filed Mar. 31, 2008. Both of these applications are incorporated herein by reference.

TECHNICAL FIELD

The present invention concerns a process for preparing pharmaceutical compositions comprising one or more active ingredients in the form of fine particles.

More particularly, the subject of the present invention is a process for producing solid pharmaceutical compositions comprising micron-size or submicron size particles of active ingredient, preferably crystalline particles, dispersed on the surface of and/or in powders of pharmaceutical excipients.

STATE OF THE PRIOR ART

Numerous active substances, particularly of human or veterinary pharmaceutical interest, are very scarcely soluble in water and aqueous biological liquids. This characteristic induces very low and often most varying bio-availability. The very low solubility of these active ingredients is a major obstacle for the pre-clinical then clinical evaluation thereof and evidently also for their use in therapeutic applications. Numerous active substances cannot therefore be efficiently administered in usual pharmaceutical forms via oral route which is the most frequent route and for which absorption of the active ingredient essentially requires the dissolution of the therapeutic dose in gastrointestinal fluids, or via other administration routes such as intravenous route for which solutions of the active ingredient in aqueous vehicles are commonly used.

Varied techniques have been researched to produce pharmaceutical forms with which it is possible to administer scarcely soluble active ingredients. For example, mention may be made of formulation techniques to produce micellar solutions, solid dispersions in which the active ingredient is dispersed in a water-soluble matrix, combination complexes between the active ingredient and cyclodextrins, lipid formulations such as self-emulsifying systems, nanoparticles of solid lipids, lipid nanocapsules and liposomes. Although used for a few commercially available pharmaceutical forms, these formulation techniques are often complex, entail several production steps and most often use organic solvents or excipients which may raise problems of toxicity and may require recourse to severe operating conditions (temperature, shear) which have a deleterious effect on the chemical or physical stability of the active ingredient.

Aside from these formulation techniques, one approach that is often efficient is to reduce the size of the particles of active substance in order to increase the rate of dissolution in biological fluids. Numerous pharmaceutical forms on the market contain micron-size particles of active ingredient i.e. particles of a few micrometers obtained for example using dry milling techniques e.g. air jet milling. As presented in a recent review by F. Kesisoglou et al. (Nanosizing—Oral formulation development and Biopharmaceutical Evaluation, published in Advanced Drug Delivery Review, Vol. 59, pp. 631-644, 2007), the production of nanoparticles of active substances also called submicron particles is a field undergoing strong recent development, in particular because it has been shown that reducing the size of particles of active ingredient down to a few hundred nanometers may allow an increase in dissolution rates with much higher gains than those obtained with micronized particles of a few micrometers due the effect of the strong increase in specific surface area, as described by the Nernst-Brunner/Noyes-Whitney equation, but also due to a theoretical increase in solubility at saturation for sizes of a few tens or hundreds of nanometers as described by the Ostwald-Freundlich equation.

The methods for obtaining nanoparticles of active substances used to produce market pharmaceutical forms are wet processes for high pressure homogenization or nano-milling using ball mills. The use of these techniques is known for producing two medicinal products, Triglide™ and Tricore™, these two products administered via oral route being pharmaceutical forms containing nanoparticles of fenofibrate. These mechanical processes lead to obtaining a dispersion of solid nanoparticles of active substances in a liquid. This liquid is frequently composed of an aqueous medium containing one or more stabilization agents to prevent the formation of aggregates and phase separation. The choice of excipients to allow the prevention of nanoparticle agglomeration or to control the growth of particles by Ostwald ripening amounts to a cumbersome, complex empirical task. Additionally, these excipients must necessarily be chosen from among pharmaceutical excipients of adapted regulatory status. For an administration route such as the parenteral route, the low quantity of available pharmaceutical excipients may lead to very difficult development of such formulations.

Although the short-term storage of dispersions of fine particles in an aqueous vehicle may be difficult on account of problems of physical or microbiological stability, the suspensions of nanoparticles produced by the above-mentioned mechanical processes are sometimes used as such for pre-clinical tests or even for initial clinical trials. On the other hand, aqueous dispersions of nanoparticles of active substances must be converted to dry forms in order to obtain a marketed pharmaceutical form of easy use and acceptable stability. This conversion can be conducted using usual drying methods such as spray drying or fluidized air bed techniques. The development of these dry formulations is often very complex since it is necessary to develop a re-dispersible dry form i.e. which, after oral administration or reconstitution in an aqueous medium, allows a dispersion of nanoparticles to be re-formed having characteristics identical to those contained before drying, which often requires the recourse to numerous formulation excipients. The production of market pharmaceutical forms from dispersions of nanoparticles of active substance in a liquid therefore necessitates cumbersome, largely empirical development work and leads to an overall manufacturing process for the medicinal product that is complex, entailing multiple steps which have a deleterious effect on the chemical or physical stability of the active ingredient and the performance of the formulation.

For the purpose of producing fine particles of active substances, precipitation or crystallization processes of these substances previously placed in solution are also known. To supplement crystallization from solutions in an organic solvent, which may raise numerous problems for active substances intended for administering to man, the precipitation of active substances from a solution in a supercritical fluid has been researched for about twenty years to produce powders of active ingredients such as presented in the review by J. Jung et al. (Particle Design Using Supercritical Fluid: Literature and Patent Survey, published in: Journal of Supercritical Fluids Vol. 20, pp. 179-219, 2001) or more recently in the review by E. Rodier et al. (<<La génération de solides divisés par voie supercritique: principes de base, considérations sur l'état d'avancement des recherches [Generating divided solids via supercritical route: basic principles, considerations on the progress of research] published in Cahiers de Formulation, Vol. 14, pp. 90-108, 2008). Compressed fluids, particularly supercritical carbon dioxide ($CO_2$) are finding an increasing number of applications for numerous processes.

To specify what is meant by a supercritical fluid, first the different states of a fluid are recalled and the properties thereof in each of these states. It is known that bodies are generally known to have three states, namely solid liquid or gas, and the changeover from one to the other is obtained by varying temperature and/or pressure; in addition to the solid state there exists the liquid state and the gas state separated by the vaporization/condensation curve; however in the Pressure-Temperature phase diagram there is point beyond which it is possible to change from the liquid state to the gas or vapour state without boiling or conversely without condensation: this point is called the critical point. A supercritical fluid is characterized either by pressure and temperature respectively higher than critical pressure and temperature for a pure body, or by a representative pressure-temperature point lying beyond the region of the critical points represented on a pressure-temperature phase diagram for a mixture; for many numerous substances it then has solvent properties having no possible comparison with those observed with this same fluid in the compressed gas state. The same applies to so-called "sub-critical" liquids i.e. liquids in a state characterized either by pressure higher than the critical pressure or by a temperature lower than the critical temperature for a pure body, or by pressure higher than the critical pressures and temperature lower than the critical temperatures of the components with respect to a mixture. The major, scalable variations of the solvent properties of supercritical fluids and the easy separation of the solvent/solute mixture by mere expansion are used moreover in numerous (solid/fluid) extraction processes, (liquid/fluid) fractionating methods and for particle generation.

It is to be noted that the physicochemical properties of carbon dioxide and its critical parameters (critical pressure: 7.4 MPa and critical temperature: 31° C.) make it the solvent of choice for numerous applications insofar as it offers the possibility of working at moderate temperature for heat-sensitive active substances, all the more so since it does not have any toxicity and is available at low cost and in large quantities. Other fluids can also be used such as nitrous oxide, light hydrocarbons having two to four carbon atoms, ethers and some halogenated hydrocarbons such as tetrafluoroethane (R134a).

For the purpose of generating particles of active substance, a process called RESS is known (Rapid Expansion of Supercritical Solutions) described in U.S. Pat. No. 4,582,731 according to which a solution of active substance in a supercritical fluid is expanded in a low pressure zone. The usual implementation of the RESS process comprises two successive operations. The supercritical fluid is contacted with the product to be atomized in an extractor and the supercritical solution thus generated is heated then expanded via an expanding device in a vessel held at a pressure that is much lower than the pressure prevailing inside the extractor. This process allows fine particles to be obtained that are dispersed in a low pressure gas stream. A particular implantation of the RESS process is also known as described in patent application WO 01/43853 in which fine powders of active substances are generated by expanding a supercritical solution through a nozzle, the said fine powders then being captured by percolating the gas stream loaded with the generated particles through a receiving bed formed of granules of a pharmaceutical excipient. The products thus generated can be used directly to manufacture tablets or to fill capsules.

One of the limitations of the RESS process lies in the fact that the supercritical solution must be brought to a high temperature before sudden expansion thereof, so that at no time is the two-phase liquid/vapour region entered into during expansion. Entry into the two-phase region effectively risks leading to partial re-dissolution of the active substance in the liquid phase. In most frequent cases, in which expansion is conducted rapidly via a capillary and can therefore be considered to be isenthalpic, upstream temperatures of the expansion device ranging from 140° C. to 200° C. are usually used for $CO_2$ which, despite the very short residence time of the supercritical solution at this temperature, may lead to triggering the degradation of heat-sensitive active ingredients.

Another possible limitation of the RESS process concerns the use of the process for active substances whose solubility in the supercritical fluid decreases with increases in temperature at the pressure at which the solution is obtained. Persons skilled in the art effectively know that the solubility of an active substance in a supercritical fluid can be represented by what is known as Chrastil's equation. This equation uses the product of two terms having antagonist effects when the temperature increases. Therefore, for some active substances, there may be a pressure and temperature range in which the solubility of the active substance in the supercritical fluid is reduced when temperature is increased. In this case, the application of the RESS process raises a problem when the extraction temperature is lower than the temperature immediately upstream of the expansion device, since the active substance may precipitate upstream or in the expansion device and cause clogging of the said device.

A review of the applications of the RESS process for the generation of submicron particles (M. Türk "Manufacture of submicron drug particles with enhanced dissolution behaviour by rapid expansion process", J. of Supercritical Fluids, Vol. 47, pp. 537-545, 2009) shows that this process applied to numerous active substances should theoretically lead to obtaining nanoparticles. The sudden expansion at a pressure close to atmospheric pressure of a solution in a supercritical fluid effectively leads to extremely high, rapid super-saturation, and hence to the precipitation of the product in the form of submicron particles dispersed in a gas stream during expansion. However, it is the production of micron particles that is often observed and not submicron particles using the RESS process, probably on account of growth and/or agglomeration of particles inside the vessel in which they are generated. To overcome this problem, variants of the RESS process have been examined. Processes designated RESAS or RESOLV are known whose principle and applications are detailed in the afore-mentioned publication by M. Türk, in which the supercritical solution is expanded in an aqueous solution containing surfactant stabilization agents which allow limited growth and agglomerating of particles of active substances, and hence the production of nanoparticles of active substances. These processes therefore lead to obtaining a dispersion of nanoparticles in an aqueous medium containing stabilization agents. The products obtained with this method are therefore comparable with those obtained using wet milling methods or high pressure homogenization and suffer from the same limitations for producing a market pharmaceutical form.

Also known is an example of a process using supercritical fluids in which expansion is operated under pressure and temperature conditions which lead to obtaining a mixture of gaseous $CO_2$ and liquid $CO_2$ at the output of the expansion nozzle, and not a stream of gaseous $CO_2$ (J. Robertson et al., "Recrystallization of organic compounds using near critical carbon dioxide", Proceedings of the $4^{th}$ International Symposium on Supercritical Fluids, May 11-14, Sendai, Japan, 1997). Those skilled in the art will understand that this very particular implementation makes it possible to avoid excessive heating of the supercritical fluid, the extraction temperature and the temperature immediately upstream of the expansion device being identical, and therefore to treat heat-sensitive active substances. This publication further teaches that the particle size of an active ingredient increases with expansion pressure, probably due to decreasing supersaturation of the fluid when it is expanded at increasing pressures and to the increase in the proportion of liquid $CO_2$ with pressure which, as expected by a skilled person on account of the risk of re-dissolution of the active substance in the liquid $CO_2$, may generate particle growth of through secondary crystallization. No examples are known for producing discrete submicron particles using this method.

There is therefore a major need for new methods to prepare nanoparticles of active substances which can easily be used for producing stable pharmaceutical forms, and advantageously without having recourse to the use of numerous excipients or numerous production steps, and which lead to obtaining nanoparticles dispersed in a liquid and further allowing application to heat-sensitive active substances.

BRIEF DESCRIPTION OF THE INVENTION

Surprisingly and unexpectedly, the inventors have shown that it is possible to produce a solid composition comprising fine micron and/or preferably submicron particles of at least one active substance dispersed on the surface of and/or in a divided solid by applying a process noteworthy in that it comprises a step to expand a solution of the said active substance in a fluid at supercritical pressure, in a chamber under pressure and temperature conditions at which part of the fluid is in liquid form during expansion, and noteworthy in that the said chamber contains a divided solid.

The process subject of the invention is of particular interest in that it allows the advantageous production of fine, micron and preferably submicron particles of heat-sensitive active substances since it does not necessitate the recourse to high temperatures before the expansion step of the supercritical solution.

The process subject of the invention is also of interest in that it allows the production of fine particles of active substances under conditions in which the heating of the supercritical solution before expansion, such as required for implementation of the RESS process, is not possible owing to the decreasing solubility with temperature of the active substance in the fluid at supercritical pressure at the chosen pressure.

The process subject of the invention is of particular interest in that it allows a solid dry product to be obtained containing microparticles or nanoparticles of active substance and therefore does not necessitate downstream conversion operations to dry form in order to produce a stable pharmaceutical form. The process subject of the invention is therefore particularly advantageous in that it allows the substitution of complex processes for manufacturing nanoparticle pharmaceutical forms, the most usual processes comprising multiple wet size-reducing steps leading to a dispersion of nanoparticles in a liquid followed by conversion to dry form.

Advantageously, the solid compositions obtained according to the process subject of the invention can be easily handled and converted to end solid forms intended for administration via oral route e.g. but not limited to capsules, tablets, orodispersible forms, sublingual or bioadhesive forms, powders to be reconstituted as drinkable suspensions, the said conversion possibly being achieved using routine pharmacotechnical unit operations well mastered by the pharmaceutical industry such as, but not limited to, mixing, compression, granulating or film-coating operations. The oral forms thus produced may be, but are not limited to, immediate release forms, controlled release forms or enteric release forms.

Advantageously the compositions obtained using the process subject of the invention may also be used to produce end forms intended to be administered via routes other than the oral route, these possibly being, but not limited to, forms for injection, for lung, nasal, rectal, vaginal or transdermal route. The solid compositions obtained using the process subject of the invention can more particularly be used with ease to produce forms for injection, intended inter alia for administration via intravenous, intramuscular, subcutaneous, intraocular or intra-articular route, administration possibly being given via short, rapid injection or by slow infusion. The solid compositions obtained with the process subject of the invention can effectively be stored in dry form having great stability, optionally after mixing with pharmaceutical excipients, and then dispersed extemporaneously in a liquid vehicle, preferably in an aqueous medium which may contain dispersion and stabilization agents, so as to produce a dispersion of fine particles for injection, preferably of submicron particles.

Advantageously the use of the process subject of the invention allows extensive limiting of the number of excipients used to produce a stable market pharmaceutical form.

Advantageously the process subject of the invention allows the production of fine and preferably submicron particles in a solid state (crystallinity and polymorphism) allowing a stable pharmaceutical form to be obtained, preferably crystalline submicron particles, more preferably crystalline particles essentially containing the most stable crystalline form.

By essentially is meant that more than 80% and preferably more than 95% of the crystalline particles are in the most stable crystalline form at the recommended storage temperature of the market pharmaceutical form.

DESCRIPTION OF THE FIGURES

FIG. 9: FIG. 4: In vitro dissolution curves (Example 3).

DETAILED DESCRIPTION OF THE INVENTION

This invention is based on the fact that it is surprising to ascertain that the expansion of a solution comprising at least one active substance solubilised in a fluid at supercritical pressure, under operating conditions leading to the presence of the fluid partly in liquid form during expansion, allows the obtaining of fine particles of active substances, and advantageously submicron particles, when the fluid is expanded in an expansion chamber comprising a divided solid.

Therefore the present invention notably concerns a process for preparing a solid composition comprising fine, micron and preferably submicron particles of at least one active substance dispersed on the surface of and/or in a divided solid, noteworthy in that it comprises a step to expand a solution of the said active substance in a fluid at supercritical pressure in a chamber under conditions of pressure and temperature at which part of the fluid is in the liquid form during expansion, and in that the said chamber contains a divided solid.

According to one preferred embodiment, the process of the invention comprises the steps of:

a) Forming a solution of the active substance in a fluid at supercritical pressure;

b) Expanding the said solution in a chamber under pressure and temperature conditions at which part of the fluid is in the liquid form during expansion;

c) Contacting the fluid thus expanded with a divided solid in the said chamber;

d) Collecting a dry product containing the said active substance in the form of fine particles, and the divided solid.

According to a further preferred embodiment, the process the invention consists of:

a) Forming a solution of the active substance in a fluid at supercritical pressure;

b) Expanding the said solution in a chamber under pressure and temperature conditions at which part of the fluid is in liquid form during expansion;

c) Contacting the fluid thus expanded with a divided solid in the said chamber;

d) Collecting a dry product containing said active substance in the form of fine particles, and the said divided solid.

Under the present invention, by the term "part of the fluid is in liquid form" it is meant that at least 1% and in increasing order of preference at least 5%, at least 10%, at least 20%, at least 30% and at least 50% of the fluid is in liquid form during expansion. According to one preferred embodiment, between 10 and 90% and most preferably between 20 and 80% of the fluid is in liquid form during expansion.

Under the present invention, the percentage of fluid in liquid form is the theoretical percentage of the fluid in liquid form at the temperature and pressure conditions of expansion. This can be determined on the basis of expansion mechanism hypotheses, for example using a pressure-enthalpy thermodynamic diagram known as the "Mollier diagram" with which it is possible, for each temperature and pressure condition of the fluid immediately upstream of expansion and for each pressure in the expansion chamber, to determine the percentage of fluid in gaseous form and the percentage of fluid in liquid form. Said diagrams can be determined for example using thermodynamic data easily accessible to those skilled in the art, such as those described by E. W. Lemmon, M. O. McLinden and D. G. Friend in "Thermophysical Properties of Fluid Systems" in the WebBook of Chemistry NIST, Standard Reference Database NIST Number 69, Eds. P. J. Linstrom and W. G. Mallard, National Institute of Standards and Technology, Gaithersburg Md., 20899 (http://webbook.nist.gov).

For reasons of clarity, it is specified that the other part of the fluid which is not in liquid form during expansion is in gaseous form.

Under the present invention, the percentage of fluid in liquid form corresponds to weight ratios between the weight of fluid in liquid form and the total weight of the fluid.

In the remainder hereof, nanoparticles or submicron particles will be used to designate particles of median size less than 1000 nm. Particles of median size less than 1000 nm are defined herein as a group of particles of which 50% have a volume median diameter of less than 1000 nm, the said volume median diameter being measured by laser particle measurement for example or by photon correlation spectroscopy.

The particles comprising an active substance obtained using the process subject of the invention are advantageously micron particles, preferably submicron particles, further preferably submicron particles of volume median diameter (dv [0.5]) less than 800 nm, more preferably of volume median diameter less than 500 nm. 90% of the fine particles preferably have a volume diameter (dv [0.9]) of less than 10 μm, more preferably less than 5 μm, further preferably less than 2 μm, still further preferably less than 1000 nm.

Under the present invention, fluid at supercritical pressure will be used to designate a fluid brought to a pressure higher than its critical pressure i.e. either a supercritical fluid properly so called or a so-called sub-critical liquid as defined above; supercritical solution will designate a solution of one or more active substances in a supercritical fluid, and solution at supercritical pressure will designate a solution of one or more active substances in a fluid at supercritical pressure.

According to one embodiment of the invention, a solution of at least one active substance is formed in a fluid at supercritical pressure. This solution at supercritical pressure is preferably produced using equipment similar to the equipment illustrated FIG. 1, in which the solid active substance in placed in a high-pressure extractor 5 and the fluid at supercritical pressure is caused to percolate inside the extractor. This embodiment corresponds to the one commonly used by those skilled in the art for supercritical fluid extraction methods from solid matrices, the active substance forming the compound to be extracted and the solid matrix being formed either of the solid active substance alone or the active substance mixed with an inert solid material. Those skilled in the art will know that the said inert material mixed uniformly with the solid active substance using suitable means under ambient conditions, chiefly allows improved contact efficacy between the fluid at supercritical pressure and the active substance, so as to guarantee the placing in solution of the active substance in the fluid at supercritical pressure in reproducible manner. In addition, the inert material may permit immobilization of the active substance and ensure efficient contact with the fluid at supercritical pressure in the particular case when the active substance which is solid under ambient conditions is in the liquid or semi-solid form under extraction conditions. As a non-limiting example, the inert material may be formed of fibrous materials, porous materials or beads preferably beads in glass, ceramic, stainless steel or zirconium oxide, or polymers of suitable diameter to ensure uniform reproducible mixing with the active substance before placing in the high-pressure extractor. Preferably, one or more elements guaranteeing the non-entrainment of particles of non-solubilised active substance at the output of the extractor will be used.

In one preferred embodiment of the process subject of the invention, the step to form the solution at supercritical pressure allows the guaranteed constant concentration of active substance in the fluid at supercritical pressure throughout the process. In this perspective, and taking inspiration from current practice in extraction methods from solid matrices, it is possible to apply the technique known to those skilled in the art as the simulated mobile bed technique in which at least three extractors are used with at least two high-pressure extractors in series throughout the duration of the technique and one extractor for the decompression, unloading, filling or pressurizing phases during such time. Advantageously, the first extractor among the extractors placed in series is the one closest to exhaustion of active substance. The use of such device allows the guaranteed constant concentration of active substance in the fluid at supercritical pressure. Additionally, provided the installation is sized according to rules of the art, the concentration of active substance in the supercritical fluid may effectively be in the region of the so-called saturation concentration corresponding to the limit solubility of the active substance in the fluid at supercritical pressure under the chosen extraction conditions.

The above-described embodiments have in common that they generally lead to a solution close to active substance saturation in the supercritical fluid at the output of the extractor.

One particular embodiment of the process subject of the invention includes mixing the solution in the fluid at supercritical pressure, before the expansion step, with a known quantity of fluid at supercritical pressure not containing any active substance, for example using a high-pressure static mixer so as to adjust the concentration of active substance in the fluid at supercritical pressure before expanding and contacting with a divided solid, in order to adjust the properties of the pharmaceutical compositions obtained with the process subject of the invention.

According to one particular embodiment, the above devices can be completed with an in-line measuring system to measure the concentration of active substance in the fluid at supercritical pressure, for example but not limited thereto a spectrophotometry method.

According to one preferred embodiment of the invention, the fluid at supercritical pressure is chosen from among carbon dioxide, nitrous oxide, alkanes such as ethane or propane, ethers such as dimethyl ether, fluorinated hydrocarbons such as tetrafluoroethane (R134a) or trifluoromethane (R23).

According to one particularly preferred embodiment, the fluid at supercritical pressure is carbon dioxide.

According to another embodiment of the invention, the fluid at supercritical pressure is formed either of a mixture of at least two of the above-mentioned fluids, or of a mixture of one of the above-mentioned fluids with at least one organic solvent advantageously chosen, but not limited thereto, from among alcohols, ketones and esters.

According to one embodiment of the process according to the invention, the fluid at supercritical pressure is carbon dioxide at a pressure of between 7.4 MPa and 200 MPa, preferably between 10 and 100 MPa, and at a temperature lower than 140° C. and in increasing order of preference at a temperature lower than 80° C., 60° C. and 40° C.

According to one preferred embodiment of the invention, the fluid at supercritical pressure is carbon dioxide at a pressure of between 25 MPa and 70 MPa, at a temperature of between 40 and 80° C.

According to one preferred embodiment of the process subject of the invention, the solution at supercritical pressure is composed of an active substance dissolved in the fluid at supercritical pressure.

According to one particular embodiment of the process subject of the invention, the solution at supercritical pressure comprises several solutes, and preferably at least two active substances or at least one active substance and a pharmaceutical excipient.

According to the process subject of the invention, the solution of active substance in the fluid at supercritical pressure is expanded in a chamber under conditions during expansion leading to the formation of a two-phase system comprising the fluid in the liquid state and the fluid in the gas state.

The temperature of the solution at supercritical pressure immediately upstream from the expansion device can be adjusted, for example and in non-limiting manner, by passing the supercritical solution through an exchanger. In one particular embodiment of the process of the invention, the adjustment of the temperature of the solution at supercritical pressure can be operated by mixing the solution at supercritical pressure originating from the high-pressure extractor with fluid at supercritical pressure at a temperature different from the temperature of the solution at supercritical pressure. Under these conditions, which those skilled in the art will identify as corresponding to a permanent operating schedule of the process of the invention, it is therefore possible to adjust simultaneously the concentration of active substance substantially below the so-called saturation concentration in the fluid at supercritical pressure and the temperature of the solution at supercritical pressure immediately upstream from the expansion device.

According to one particular embodiment of the invention, the temperature of the fluid at supercritical pressure during the formation step of the solution at supercritical pressure is identical to the temperature immediately upstream from the expansion device.

According to another embodiment of the invention, the temperature of the fluid at supercritical pressure during the formation step of the solution at supercritical pressure is substantially lower than the temperature immediately upstream from the expansion device.

According to one embodiment of the method of the invention, the solution at supercritical pressure is expanded in a chamber by means of an expansion device formed of a spray nozzle, a tube, an orifice pierced in a plate of narrow thickness, an element in solid sintered material, a valve with controlled opening, or by any other device known to those skilled in the art.

According to one preferred embodiment, the expansion device is formed of a capillary tube characterized by a length to inner diameter ratio of more than 20 and preferably more than 100.

Irrespective of the expansion device used, those skilled in the art may easily determine the operating conditions of the process leading to the formation of part of the fluid in the liquid state during expansion, for example by examining thermodynamic diagrams such as the so-called "Mollier diagrams" on the basis of expansion mechanism hypotheses, the said expansion possibly being considered as mostly isenthalpic or isentropic depending on the chosen expansion device, or during preliminary tests of the apparatus used to apply the process e.g. without being limited thereto by measuring the temperature immediately downstream from the expansion device in the expansion chamber, or by measuring a physical magnitude immediately downstream of this device which allows the conclusion that part of the fluid is present in liquid form.

According to the process subject of the invention, the pressure in the expansion chamber is held at a value leading to obtaining a two-phase gas-liquid medium during expansion, in relation to the pressure and temperature conditions of the solution at supercritical pressure immediately upstream from the expansion device. This pressure can be determined by a skilled person using thermodynamic diagrams for example, such as pressure-enthalpy diagrams. The pressure can be maintained at this value by means of a valve regulating upstream pressure located downstream of the expansion chamber or using any device known to a skilled person which provides pressure control under these operating conditions.

The process subject of the invention is preferably conducted using carbon dioxide with a pressure in the expansion chamber held at between 0.52 and 7.4 MPa, preferably between 1 and 6.5 MPa.

According to one preferred embodiment of the invention, part of the fluid which is in the liquid state during expansion is vaporized in the expansion chamber by providing enthalpy using any means known to persons skilled in the art, preferably by heating the walls of the chamber or by adding a fluid at a rate and temperature allowing the required enthalpy to be achieved.

According to one preferred embodiment, the fluid added to provide enthalpy is identical to the fluid used for the formation of the solution at supercritical pressure.

According to one preferred embodiment of the invention, the fluid in the liquid state is fully vaporized inside the expansion chamber and is therefore fully in the gaseous state when it leaves the said chamber.

According to the process subject of the invention, the fluid at supercritical pressure in which at least one active substance is solubilised, is expanded in a chamber comprising a divided solid. Therefore, the said divided solid comes into full or partial contact with the expanded fluid partly in the liquid state. According to one preferred embodiment of the invention, the said divided solid comprises a pharmaceutical excipient.

According to one preferred embodiment of the invention, the expanded fluid is contacted with the divided solid using any means known to those skilled in the art allowing the uniform distribution of the two-phase gas-liquid mixture of the fluid on the divided solid, and hence leading to uniform distribution of the active substance in the end solid, dry composition.

According to a still further preferred embodiment, the positioning of the expansion device and the geometric configuration of the expansion chamber allow agitation of the divided solid to be obtained solely via the ejection velocity of the expanded fluid.

Advantageously, the expansion chamber is equipped with a mechanical agitation system if needed for agitation of the divided solid.

According to another embodiment of the process of the invention, the expansion chamber is equipped with a device which, without complete depressurization of the said chamber, allows the feeding of divided solid and the withdrawal of the solid composition comprising the divided solid and the active substance. This feeding and withdrawal are advantageously operated at regular time intervals and preferably continuously. Said device allows the use of an expansion chamber of substantially reduced volume compared with discontinuous application of the process.

According to one particular embodiment of the invention, the divided solid is a powder or granular material composed of at least one pharmaceutical excipient.

According to one particularly advantageous embodiment of the invention, the divided solid is formed of particles of at least one excipient acceptable for administration via oral route, and preferably chosen from among excipients known to persons skilled in the art as having favourable properties for producing solid oral forms such as tablets or capsules. The excipients for oral administration are advantageously chosen from among sugars such as lactose or sucrose, polysaccharides such as microcrystalline cellulose, derivatives of cellulose or starch, polyols such as mannitol, solid lipids and waxes, solid homopolymers and copolymers such as polyesters, polyethylene glycols, poloxamers, polyvinylpyrrolidones and derivatives, inorganic compounds such as silica.

According to another advantageous embodiment of the process subject of the invention, the divided solid is formed of a powder composed of an excipient soluble in aqueous media and acceptable for administration via injection route such as, but not limited to, the intravenous, intramuscular, intra-articular or intra-ocular routes. The excipients for administration via injection route are advantageously chosen from among salts such as sodium chloride, sugars such as trehalose or sucrose for example, polyols such as mannitol for example, polysaccharides, bio-absorbable polymers, proteins such as albumin.

According to one advantageous embodiment of the process of the invention, the divided solid is formed of particles of pharmaceutical excipient having a mean size of between 50 and 2000 micrometers, preferably between 200 and 600 micrometers.

According to one advantageous embodiment of the process subject of the invention, the weight ratio between the active substance and the divided solid is between 0.1 and 25%, and preferably between 0.5 and 10%.

Figure 1:
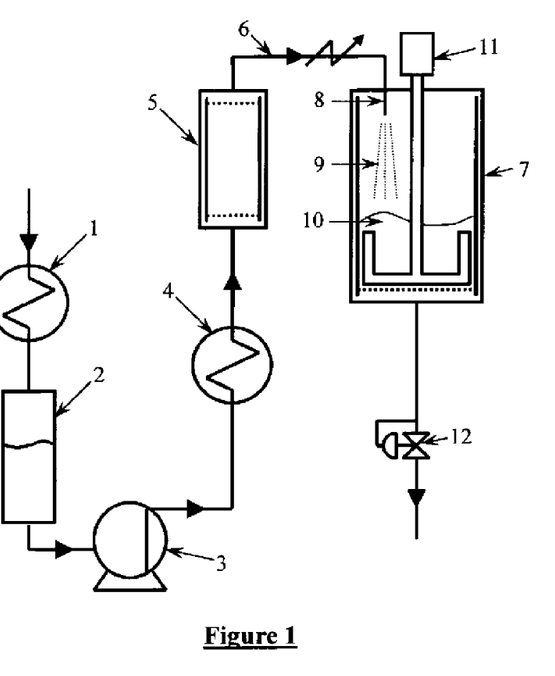
FIG. 1: Schematic of the device used to implement the process of the invention.
Figure 2:
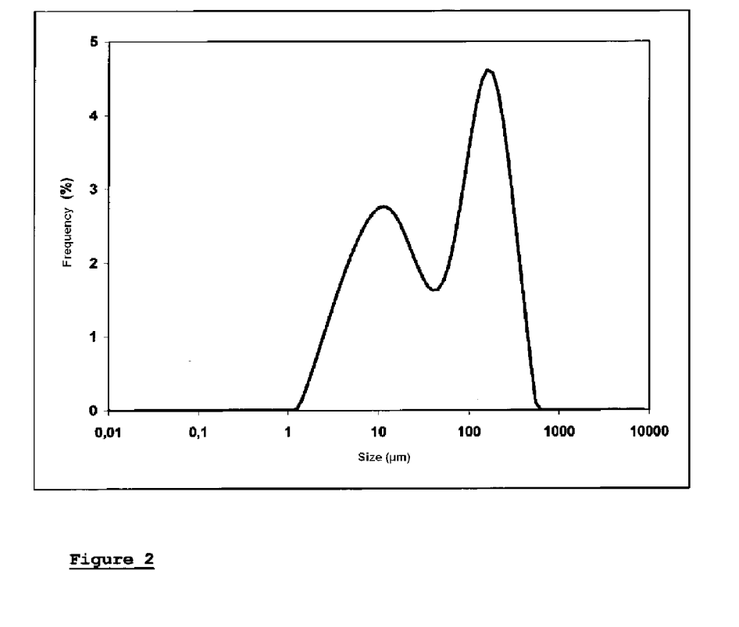
FIG. 2: Profile of volume particle-size distribution of particles of active substance produced with Test 1-1 (Example 1).
Figure 3:
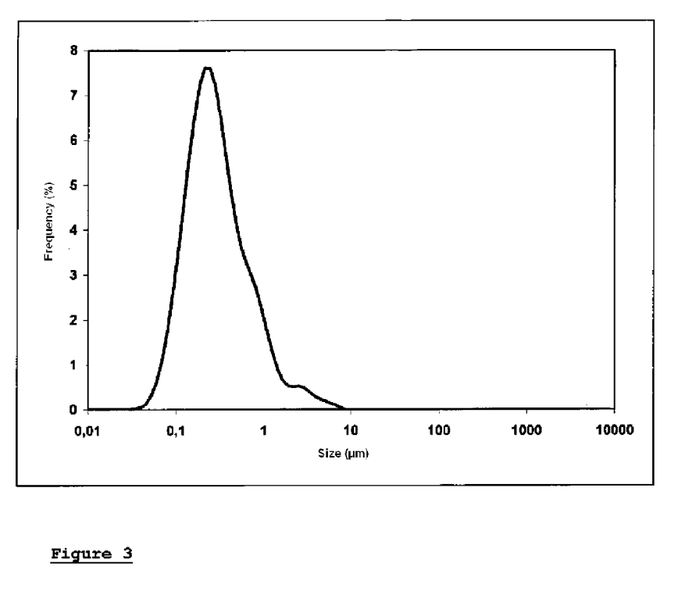
FIG. 3: Profile of volume particle-size distribution of particles of active substance produced with Test 1-2 (Example 1).
Figure 4:
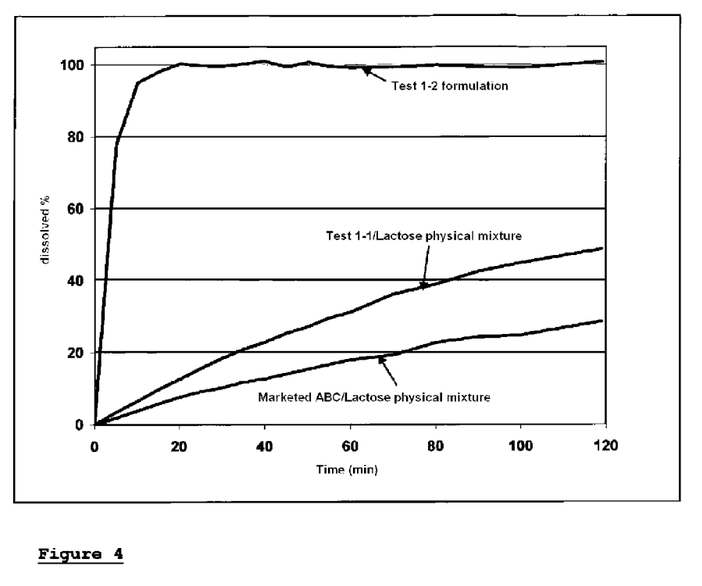
FIG. 4: In vitro dissolution curves (Example 1).

According to one preferred embodiment of the process, a device is used such as described in FIG. 1. The active substance, optionally mixed with an inert material, is placed in an extraction cell (tube with sintered stainless steel end caps to prevent entrainment of the product by the fluid). This cell is placed inside an extraction autoclave 5 heated to the chosen extraction temperature. The fluid is pumped 3 from the storage 2 and passes through a heat exchanger 4 set at the desired extraction temperature before entering the extraction autoclave. The solution of product solubilised in the fluid at supercritical pressure leaving the extraction autoclave is sent to an expansion chamber 7 in which the solution is suddenly expanded at a given temperature and pressure through a nozzle 8, the said nozzle being formed of a long tube or orifice pierced by laser in a plate of narrow thickness, and preferably a capillary tube formed by a tube whose length to diameter ratio is greater than 100. A heating device 6 is used to regulate the temperature of the fluid immediately upstream of the expansion device. Under the operating conditions chosen according to the invention, part of the fluid is in liquid form during expansion. Also, the pressure in the expansion chamber is held at a determined value by means of an upstream pressure regulator valve 12. This regulator valve allows adjustment of the operating conditions inside the expansion chamber independently of the temperature immediately upstream of the expansion device regulated by the heating device 6.

The expansion chamber contains a collector basket closed by a filter in which a powder of pharmaceutical excipient 10 is placed before start-up of the process. According to one particular embodiment of the process, an agitator device 11 is used to homogenize the content of the expansion chamber when the process is set in operation.

Also, according to one preferred embodiment of the process, the expansion chamber is heated to a temperature chosen so that under the applied operating conditions at least part of the fluid in the liquid state is able to be vaporized before leaving the expansion chamber. After passing through the regulator valve 12, the fluid is then evacuated to the atmosphere or optionally re-compressed and recycled as is known in the art.

EXAMPLES

The following examples of embodiment are given as non-limiting illustrations of the process according to the invention

Example 1

Production of an Active Substance/Lactose Formulation

The process of the invention is conducted on equipment corresponding to the layout described in FIG. 1 to produce a formulation of submicron particles of an active substance and lactose, with a targeted weight percent content of active substance of 5%.

10 g of active substance mixed with about 800 g of glass beads 1 mm in diameter are arranged in a 1.5 L extraction basket. The said basket is placed inside the extraction autoclave 5 heated to a temperature of 50° C. After a start-up step, carbon dioxide in the supercritical state brought to a pressure of 28 MPa via the pump 3 at a rate of 5 kg/h and to a temperature of 50° C. via the exchanger 4, is percolated through the extraction basket to extract the active substance. The solution of active substance in supercritical carbon dioxide thus formed is expanded through a spray nozzle 8 formed of a capillary in polyetheretherketone (PEEK) of inner diameter 170 μm and length adapted to the working pressure and flow rate. The expansion chamber 7 of effective inner volume of 545 mL is heated to 50° C. The temperature of the supercritical solution immediately upstream of the nozzle is set at 50° C. via the heating device 6. The pressure inside the expansion chamber is set at 40 bars via an upstream pressure automatic regulator valve 11. Having regard to the conditions of temperature and pressure immediately upstream of the spray nozzle and to the set pressure inside the expansion chamber, and bearing in mind that the type of nozzle used allows expansion to be considered to be near-isenthalpic, it is possible to determine in a pressure-enthalpy diagram of carbon dioxide that a two-phase mixture of liquid carbon dioxide and gaseous carbon dioxide is formed immediately downstream from the nozzle with a weight proportion of liquid carbon dioxide of about 63%. After an operating time of three hours, the $CO_2$ pump is stopped and the pressure in the chamber is gradually reduced down to atmospheric pressure in about 30 minutes before collecting the product.

A first test (Test 1-1) was conducted without any lactose in the expansion chamber.

The second test (Test 1-2) was conducted with 50.02 g of lactose (Tablettose 80) initially placed in the expansion chamber and held under mechanical agitation at 60 rpm throughout the entire duration of the test.

Results

Test 1-1 led to collecting 1.82 g of white powder strongly adhering to the wall of the collection basket in the expansion chamber.

Test 1-2 led to collecting 51.67 g of active substance/lactose formulation in the form of a free-flowing powder and of similar appearance to the lactose such as received. Weighing of the extraction basket after the test showed that 2.64 g of active substance had been extracted i.e. a global collected formulation yield of 98% and a theoretical weight percent content of active substance in the formulation of 5.01%. The assay of 5 formulation samples by high performance liquid chromatography showed that the actual weight percent content of active substance in the formulation was 4.86%. This experimental weight percent content corresponds to a collection yield of active substance during the operation of 97%. In addition, the coefficient of variation of the weight percent content measured for the 5 samples was 2.5%, indicating highly uniform distribution of the active substance in the formulation In both tests, analysis by high performance liquid chromatography indicated good stability of the active substance throughout the process, the purity and related substance profile being similar to those of the starting product in both cases.

Characterization of the solid state of the particles of active substance in the active substance/lactose formulation, by scanning differential enthalpy analysis and X-ray diffraction, showed that the particles of active substance are crystalline and in a crystalline form similar to that of the product such as received.

Analysis of the size of the particles of active substance in both tests was performed by wet mode laser particle-size measurement after dispersion of the particles in a solution of water saturated with active substance at ambient temperature in the presence of Tween 20 and after dissolution of any particles of excipient. Dispersion was achieved by passing through an ultrasound bath for 3 min before placing the dispersion in the measuring apparatus. The profiles of volume particle-size distribution for both tests are given in FIG. 2 for Test 1-1 and in FIG. 3 for Test 1-2 respectively.

The results obtained for Test 1-1 evidence bimodal particle-size distribution with the first distribution mode centred at around 10 μm and the second mode centred at around 200 μm i.e. particle sizes far removed from the technical problem subject of the process of the invention. In addition, this same analysis performed on 3 separate samples further showed that the sample of active substance alone has a size distribution that is scarcely homogeneous with an average median diameter (diameter corresponding to the 50% line of the volume-accumulated distribution curve) of 60.7 μm for the 3 samples with a coefficient of variation of 19.9%.

For Test 1-2, it appears that the particle sizes of active substance in the active substance/lactose formulation follow a single-mode distribution centred at between about 250 and 350 nm. Particle size analysis conducted on 3 separate samples indicated that the particle-size distribution of active substance in the formulation is very homogeneous with an average median diameter of 282 nm and a coefficient of variation of 1.5%.

For the purpose of performing in vitro dissolution tests on apparatus of USP I type, the formulation obtained with Test 1-2 and two physical mixtures of active substance with lactose, one with the active substance such as commercially obtained and the other with the active substance as obtained after Test 1-1, were packed in capsules (LGA, size 0, translucent, code 000020) in a quantity equivalent to 5 mg of active substance. The dissolution medium was formed of a 0.6% SDS solution at a temperature of 37° C. and the basket rotation speed was set at 80 rpm. The samples were analyzed using HPLC-UV after filtering. The in vitro dissolution profiles given in FIG. 4 show that the formulation obtained with Test 1-2 has largely improved dissolution kinetics compared with the physical mixtures, about 95% of active substance being dissolved after 10 min against less than 10% for the physical mixtures.

This example shows that the process subject of the invention allows an active substance/lactose formulation to be obtained in which the active substance is uniformly distributed chiefly in the form of nanoparticles with, in addition, very largely improved dissolution kinetics of the active substance in an aqueous medium.

Example 2

Production of a Nifedipine/Mannitol Formulation

The process of the invention was conducted on equipment corresponding to the layout described in FIG. 1 to produce a Nifedipine/Mannitol formulation having a targeted weight percent content of nifedipine of 5%.

1.5 g of nifedipine mixed with about 20 g of glass beads 1 mm in diameter are placed in a 20 mL extraction basket. The said basket is placed inside the extraction autoclave 5 heated to a temperature of 40° C. After a start-up step, carbon dioxide in the supercritical state brought to a pressure of 25 MPa via the pump 3 at a rate of 2 kg/h and to a temperature of 40° C. via the exchanger 4, is percolated through the extraction basket to extract the nifedipine. The solution of nifedipine in supercritical carbon dioxide thus formed is expanded through a spray nozzle 8 formed of a capillary in polyetheretherketone (PEEK) of inner diameter 150 μm and length adapted to the working pressure and flow rate. The expansion chamber 7 of effective inner volume 310 mL is heated to 40° C. The temperature of the supercritical solution immediately upstream of the nozzle is set at 105° C. via the heating device 6. The pressure inside the expansion chamber is set at 30 bars via an automatic upstream pressure regulator valve 11. Having regard to the temperature and pressure conditions immediately upstream of the spray nozzle and to the set pressure inside the expansion chamber, and bearing in mind that the type of nozzle used allows the expansion to be considered near-isenthalpic, it is possible to determine in a pressure-enthalpy diagram of carbon dioxide that a two-phase mixture of liquid carbon dioxide and gaseous carbon dioxide is immediately formed downstream of the nozzle with a weight proportion of liquid carbon dioxide of about 6%.

After 4 hours' operation, the $CO_2$ pump is stopped and the pressure in the chamber gradually reduced down to atmospheric pressure in about 30 minutes before collecting the product.

A first test (Test 2-1) was carried out without any mannitol in the expansion chamber.

The second test (Test 2-2) was conducted with 25.00 g of mannitol (Pearlitol 200 SD) initially placed in the expansion chamber and held under mechanical agitation at 120 rpm throughout the entire duration of the test.

Results

Test 2-1 led to collecting 0.85 g of white powder chiefly deposited on the filter placed at the bottom of the collection basket in the expansion chamber.

Test 2-2 led to collecting 23.72 g of nifedipine/mannitol formulation in the form of a free-flowing powder and of appearance similar to that of mannitol alone. Weighing of the extraction basket after the test showed that 1.07 g of nifedipine had been extracted i.e. an overall collection yield of the formulation of 91% and a theoretical weight percent content of nifedipine in the formulation of 4.10%. Using UV spectrophotometry on 5 samples it was determined that the actual weight percent content of nifedipine in the formulation was 3.89%. This actual weight percent content corresponds to a collection yield of nifedipine during the process of 95%. Additionally, it was found that the coefficient of variation of the weight percent content measured for the 5 samples was 0.5% which indicates very uniform distribution of nifedipine in the formulation.

Analysis by high pressure liquid chromatography indicated good stability of nifepdipine throughout the process for both tests with a related substance titre and profile similar to those of the starting product in both samples.

Analysis of nifedipine particle size for both tests was performed by wet mode laser particle-size measurement after dispersion of the particles in a solution of water saturated with nifedipine at ambient temperature in the presence of Tween 20 and after dissolution of any excipient particles. The dispersion of nifedipine particles was performed manually by adding a solution of Tween 20 in water to a flask in which the test product was previously placed, followed by manual upturning of the reconstitution flask i.e. following a protocol close to those commonly used for extemporaneous reconstitution of forms for injection. The profiles of particle-size distribution obtained for both tests are given in FIG. 5 for Test 2-1 and in FIG. 6 for Test 2-2 respectively.

Figure 5:
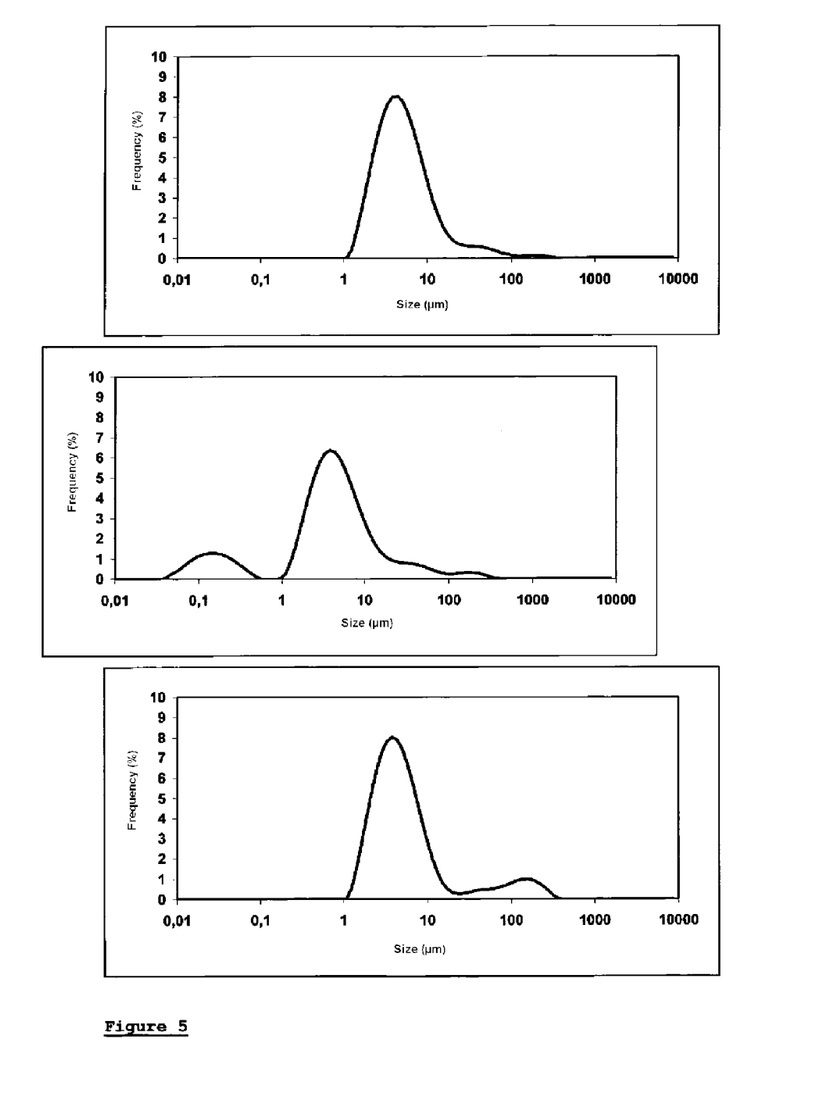
FIG. 5: Comparison, between 3 samples, of the profiles of volume particle-size distribution for particles of nifedipine produced with Test 2-1 (Example 2).

The results obtained for Test 2-1 evidence very large heterogeneity of size distributions for the 3 samples taken from the sample of nifedipine collected at the end of the test, with distribution that is either single-mode or bimodal even trimodal. However, for the 3 samples it was possible to distinguish a main peak in size distribution centred at around 4 μm.

Figure 6:
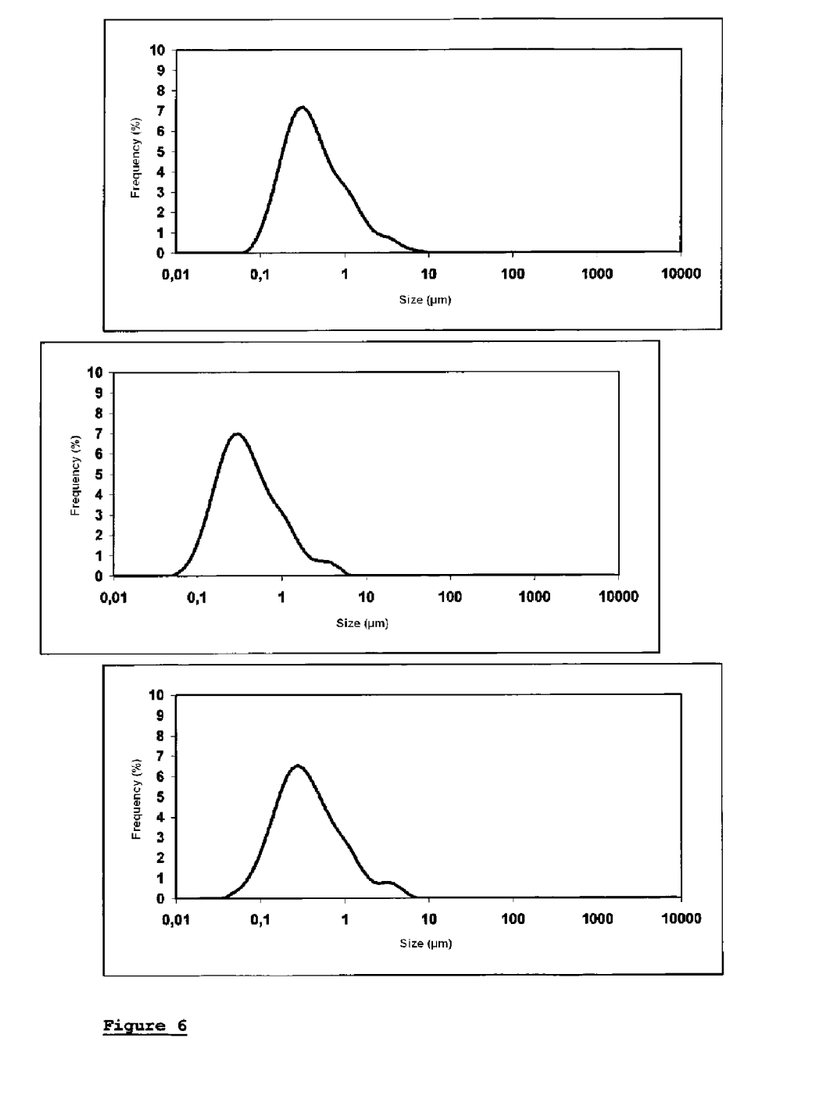
FIG. 6: Comparison, between 3 samples, of the profiles of volume particle-size distribution for particles of nifedipine produced with Test 2-2 (Example 2).
Figure 7:
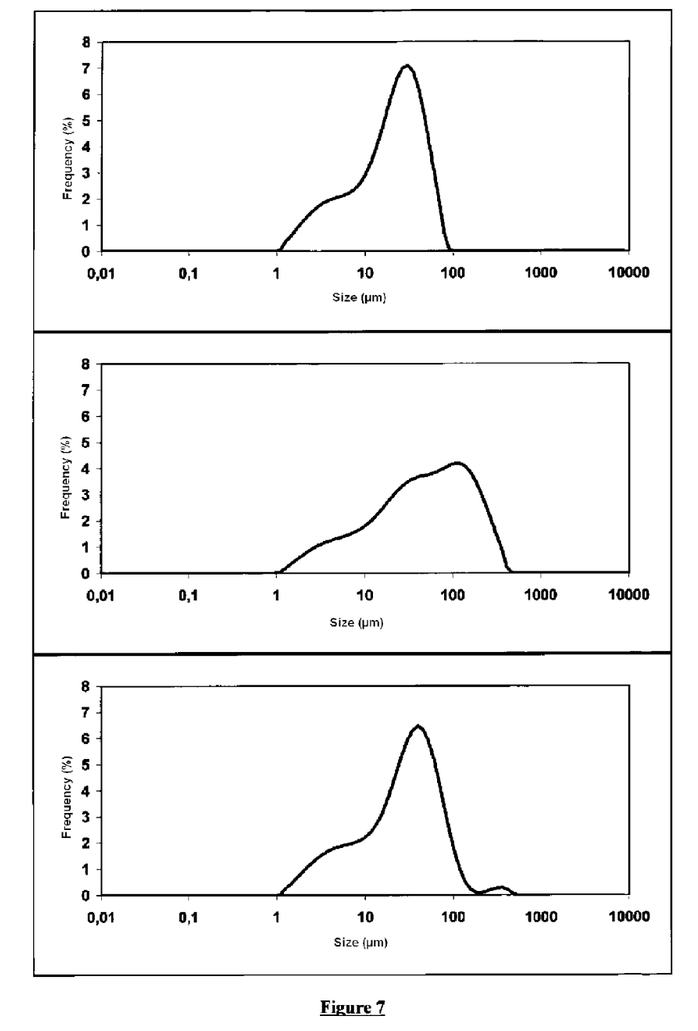
FIG. 7: Profile of volume particle-size distribution of particles of sirolimus produced with Test 3-1 (Example 3).
Figure 8:
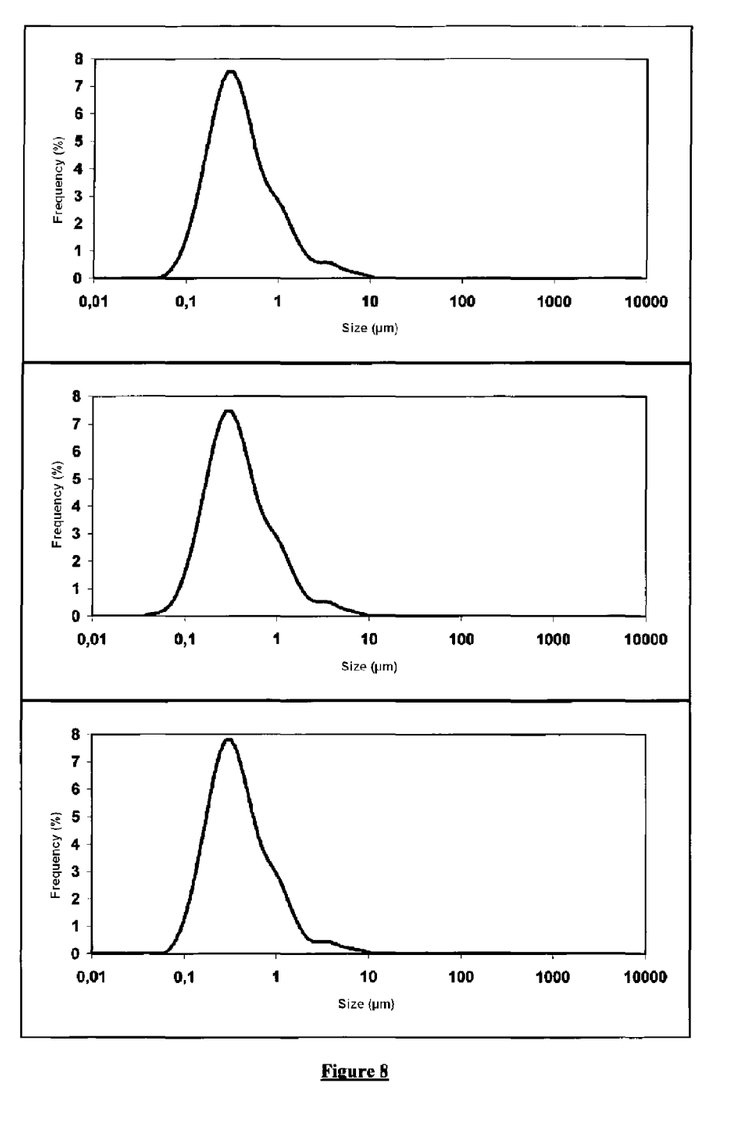
FIG. 8: Profile of volume particle-size distribution of particles of sirolimus produced with Test 3-2 (Example 3).
Figure 9:
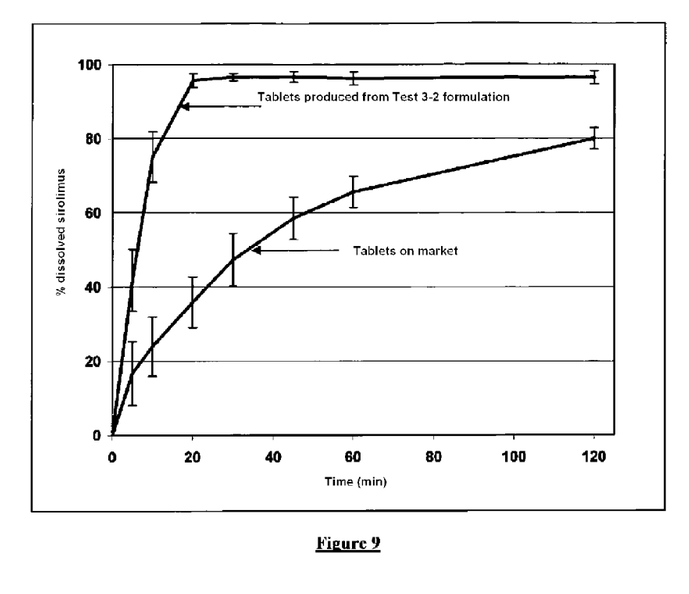

For Test 2-2 the particle sizes of nifedipine in the Nifedipine/Mannitol formulation follow near single-mode distribution centred at around 300 nm. Particle size analysis conducted on 3 separate samples indicated that the size distribution of nifedipine particles in the formulation was very homogeneous with an average median diameter of 0.39 μm and coefficient of variation of 7.1%. It is to be noted that the homogeneity of nifedipine particle-size distributions in the formulation and the value of the coefficient of variation are fully acceptable taking into account the low reproducibility of the manual dispersion mode used. Particle size measurement by photon correlation spectroscopy confirmed the obtaining of submicron nifedipine particles in Test 2-2.

This example therefore shows that the process subject of the invention allows a Nifedipine/Mannitol formulation to be obtained in which nifedipine is homogeneously distributed and in the form of mainly submicron nifedipine particles.

Example 3

Production of a Sirolimus/Lactose Formulation

The process of the invention was conducted on equipment corresponding to the layout described in FIG. 1 for the production of Sirolimus/Lactose formulations having a targeted weight percent content of Sirolimus of 2%.

1.25 g of sirolimus mixed with about 20 g of glass beads 1 mm in diameter are placed in a 20 mL extraction basket. The said basket is placed inside the extraction autoclave 5 heated to a temperature of 60° C. After a start-up step, carbon dioxide in the supercritical state brought to a pressure of 33 MPa via the pump 3 at a rate of 2 kg/h and to a temperature of 60° C. via the exchanger 4, is percolated through the extraction basket to extract the sirolimus. The solution of sirolimus in the supercritical carbon dioxide thus formed is expanded through a spray nozzle 8 formed of a capillary in polyetheretherketone (PEEK) of inner diameter 127 μm and length adapted to working pressure and flow rate. The expansion chamber 7 of effective inner volume 310 mL is heated to 60° C. The temperature of the supercritical solution immediately upstream from the nozzle is set at 60° C. via the heating device 6. The pressure inside the expansion chamber is set at 30 bars via an automatic upstream pressure regulator valve 11. Having regard to the temperature and pressure conditions immediately upstream from the spray nozzle and the pressure set in the expansion chamber, and bearing in mind that the type of nozzle used allows the expansion to be considered near-isenthalpic, it is possible to determine in a pressure-enthalpy diagram of carbon dioxide that a two-phase mixture of liquid carbon dioxide and gaseous carbon dioxide is formed immediately downstream from the nozzle with a weight proportion of liquid carbon dioxide of about 51%.

After 5 hours' operation, the $CO_2$ pump is stopped and the pressure inside the chamber is gradually reduced down to atmospheric pressure in about 30 minutes before collecting the product.

A first test (Test 3-1) was performed without any lactose inside the expansion chamber.

The second test (Test 3-2) was conducted with 49.17 g of lactose (Pharmatose DCL 21) initially placed in the expansion chamber and held under mechanical agitation at 120 rpm throughout the entire duration of the test.

Results

Test 3-1 led to collecting 0.55 g of white powder of which part strongly adhered to the wall, but also in the form of fairly coarse particles deposited on the filter in the collection basket placed inside the expansion chamber.

Test 3-2 led to collecting 49.77 g of sirolimus/lactose formulation in the form of free-flowing powder and of similar appearance to that of lactose alone. Assay by high performance liquid chromatography of 5 samples determined that the actual weight percent content of sirolimus in the formulation was 2.0% with a coefficient of variation of the weight content measured for the 5 samples of 2.3%, which indicates very uniform distribution of sirolimus in the formulation.

Analysis by high performance liquid chromatography indicated good stability of the sirolimus throughout the process in both tests with a related substance titre and profile similar to those of the starting product in both samples.

Characterization of the solid state of the sirolimus particles in the sirolimus/lactose formulation by scanning differential enthalpy analysis showed that the sirolimus particles are crystalline and in a crystalline form similar to that of the product such as received i.e. the most stable crystalline form.

Analysis of sirolimus particle size for both tests was carried out by wet mode laser particle measurement after dispersion of the particles in a solution of water saturated with sirolimus at ambient temperature in the presence of Tween 20 and after dissolution of any particles of excipient. Dispersion was obtained by passing through an ultrasound bath for 3 min before placing the dispersion in the measuring apparatus. The profiles of particle-size distribution obtained for both tests are given in FIG. 7 for Test 3-1 and in FIG. 8 for Test 3-2 respectively.

The results obtained for Test 3-1 evidence extensive heterogeneity of size distributions for the 3 samples taken from the sample of sirolimus collected at the end of the test. For the 3 samples it was nevertheless possible to determine a common peak in size distribution centred at between 30 and 40 μm. It is to be noted that for one of the samples the measured particle sizes were particularly high with about 30% of particles having a volume equivalent diameter of more than 100 μm. This measurement is coherent with visual observation of the sample which showed the presence of very coarse particles in the sample.

For Test 3-2 the particle sizes of sirolimus in the Sirolimus/Lactose formulation followed near single-mode distribution centred at around 300 nm. Particle size analysis conducted on 3 separate samples indicated that the distribution of sirolimus particle sizes in the formulation was very homogeneous with an average median diameter of 0.37 μm and coefficient of variation of 1.1%. Particle size measurement by photon correlation spectroscopy confirmed the obtaining of submicron sirolimus particles in Test 3-2.

Tablets containing 2 mg of sirolimus were produced from the formulation obtained after Test 3-2 for the purpose of comparison thereof during in vitro dissolution tests with commercially available Rapamune® 2 mg tablets. The in vitro dissolution tests were conducted using apparatus of USP I type with a dissolution medium of 0.4% Lauryl Sodium Sulphate solution at a temperature of 37° C. and basket rotation speed set at 40 rpm. The samples were analyzed by HPLC-UV after filtering. The in vitro dissolution profiles given in FIG. 9 (mean values for 6 tablets for each curve) show that the tablets produced from the formulation obtained after Test 3-2 have much largely improved dissolution kinetics compared with the marketed tablets, on average with about 75% of sirolimus dissolved after 10 min against about 25% for the tablets on the market.

This example therefore shows that the process subject of the invention allows the obtaining of a Sirolimus/Lactose formulation in which sirolimus is distributed homogeneously and chiefly in the form of submicron sirolimus particles. In addition, this Sirolimus/Lactose formulation allowed tablets to be produced which show largely improved dissolution kinetics compared with commercially available tablets.

The invention claimed is:

1. A Process for preparing a solid composition containing fine, Micron and submicron particles of at least one active substance, the particles being at least one of dispersed on the surface of a divided solid and dispersed in the divided solid wherein the process: preparing a solution of the at least one active substance in a supercritical fluid; expanding the solution of the at least one active substance in a supercritical fluid at supercritical pressure in a chamber under conditions of pressure and temperature at which part of the supercritical fluid is in liquid form during expansion, containing the divided solid; wherein the supercritical fluid a supercritical pressure is carbon dioxide at a pressure of between 7.4 MPa and 200 MPa and at a temperature lower than 140° C.

2. The process according to claim 1, further comprising:

a) forming a solution of at least one active substance in a supercritical fluid at supercritical pressure, before expanding the said solution in the chamber under the conditions of pressure and temperature at which part of the supercritical fluid is in liquid form during expansion;

b) contacting the supercritical fluid thus expanded with the divided solid in the chamber; and c) collecting a dry product, containing the at least one active substance in the form of fine particles, and the divided solid.

3. The process according to claim 2, further comprising:

a) forming a solution of at least one active substance in a supercritical fluid at supercritical pressure, before expanding the solution in the chamber under the conditions of pressure and temperature at which part of the supercritical fluid is in liquid form during expansion;

b) contacting the supercritical fluid thus expanded with the divided solid in the chamber; and c) collecting a dry product, containing the said at least one active substance in the form of fine particles, and the divided solid.

4. The process according to claim 1, wherein the supercritical fluid at supercritical pressure is carbon dioxide, and the pressure in the chamber is between 0.52 and 7.4 MPa.

5. The process according to claim 1, wherein the temperature at which part of the supercritical fluid is in liquid form during expansion is the temperature immediately upstream from the chamber.

6. The process according to claim 1, wherein the part of the supercritical fluid which is in the liquid state during expansion is vaporized in the chamber.

7. The process according to claim 1, wherein an entirety of the supercritical fluid which is in the liquid state during expansion is vaporized in the chamber.

8. The process according to claim 1, wherein the divided solid is one of a power and a granular material formed of at least one pharmaceutically acceptable excipient.

9. The process according to claim 8, wherein the at least one pharmaceutically acceptable excipient is an hydrophilic excipient.

10. The process according to claim 8, wherein the at least one pharmaceutically acceptable excipient is formed of a powder composed of an excipient soluble in aqueous media.

11. The process according to claim 8, wherein the at least one pharmaceutically acceptable excipient is selected from the group consisting of sugars, polysaccharides, derivatives of cellulose, derivatives of starch, polyols, solid lipids and waxes, solid homopolymers and copolymers, polyvinylpyrrolidones and derivatives and inorganic compounds.

12. The process according to claim 8, wherein particles of the at least one pharmaceutically acceptable excipient have a mean size of between 50 and 2000 μm.

13. The process according to claim 8, wherein a weight proportion of the at least one active substances relative to the at least one pharmaceutically acceptable excipient is between 0.1 and 25%.

14. The process according to claim 1, further comprising collecting a solid pharmaceutical composition containing particles of median size smaller than 1000 nm.

15. The process according to claim 1, further comprising collecting a solid pharmaceutical composition containing essentially crystalline particles of the at least one active substance.

16. The process according to claim 15, wherein said crystalline particles of the at least one active substance are essentially composed of a most stable crystalline form.

* * * * *